United States Patent [19]

Kurtz et al.

[11] 4,240,750

[45] Dec. 23, 1980

[54] AUTOMATIC CIRCUIT BOARD TESTER

[76] Inventors: Robert L. Kurtz, 10109 Bluff Dr.; William A. Hurd, 2107 Shannonhouse Rd., both of Huntsville, Ala. 35803

[21] Appl. No.: 947,870

[22] Filed: Oct. 2, 1978

Related U.S. Application Data

[63] Continuation of Ser. No. 752,784, Dec. 20, 1976, abandoned.

[51] Int. Cl.³ .............................................. G01B 11/00
[52] U.S. Cl. .................................... 356/394; 356/398; 356/237
[58] Field of Search .................. 356/71, 237, 394, 398

[56] References Cited

U.S. PATENT DOCUMENTS

| | | | |
|---|---|---|---|
| 3,753,617 | 8/1973 | Ehrat ..................................... | 356/398 |
| 3,909,602 | 9/1975 | Micka ..................................... | 356/237 |
| 4,065,212 | 12/1977 | Belleson et al. ....................... | 356/398 |

Primary Examiner—John K. Corbin
Assistant Examiner—R. A. Rosenberger
Attorney, Agent, or Firm—C. A. Phillips

[57] ABSTRACT

An automatic printed circuit board tester in which a laser beam is directed onto and scanned around solder pads and foil regions of a printed circuit board, and errors in structure are determined by detecting patterns of scattered light and comparing these patterns with similarly obtained ones from a properly constructed board.

2 Claims, 3 Drawing Figures

AUTOMATIC CIRCUIT BOARD TESTER

This is a continuation of application Ser. No. 752,784 filed Dec. 20, 1976, now abandoned.

BACKGROUND OF THE INVENTION

1. Field of the Invention

This invention relates to systems for determining the accuracy of wiring, component insertion, and soldering onto a printed circuit board, and particularly to an automatic means of testing for such accuracy.

2. General Description of the Prior Art

Printed circuit boards are typically checked at several stages of manufacture in order that defects can be caught at as early a stage as possible to minimize corrections that have to be made and to avoid discarding finished or near-finished boards wherein errors are caught too late for easy, and thus inexpensive, correction. This, of course, requires a considerable effort, often involving both visual and electrical inspection. The applicants have been informed that there badly exists the need for some automated system for rapidly and accurately checking boards at critical stages of production. Some of the typical problems faced in the production manufacture of these printed circuit boards are:

1. Verification of the locations (X and Y coordinates) and diameter of the perforated holes in boards.
2. Component location and identification of component.
3. Lead penetration.
4. Lead crimp direction.
5. Unintended solder bridges connecting integrated circuits or across foil.
6. Solder joint reliability.
7. Lead depth below board.
8. Cracks in printed circuit boards.
9. Foil integrity.

Ideally, there would be provided an automatic means for rapidly and accurately checking boards for one or more of the above stated conditions at selected and critical stages of production. Accordingly, it is an object of this invention to provide such a system.

SUMMARY OF THE INVENTION

In accordance with the invention, a printed circuit board is placed in a holding fixture and a fine spot of light from a laser is scanned or moved across it, employing circular, linear, spiral, cruciform, or rectangular scanning, or a combination of these, to produce desired reflections or indications of scattered light indicative of critical structural conditions or defects. The location of a particular incident of monitored reflection or scattering of light and the intensity of it, or a change in intensity of it, are as a combination compared with a predetermined criteria, and where a difference exists, an error in construction is indicated. This process requires seconds to accomplish, and is both cheaper and more accurate than previously practiced inspection.

DETAILED DESCRIPTION OF THE INVENTION

Figure 1:
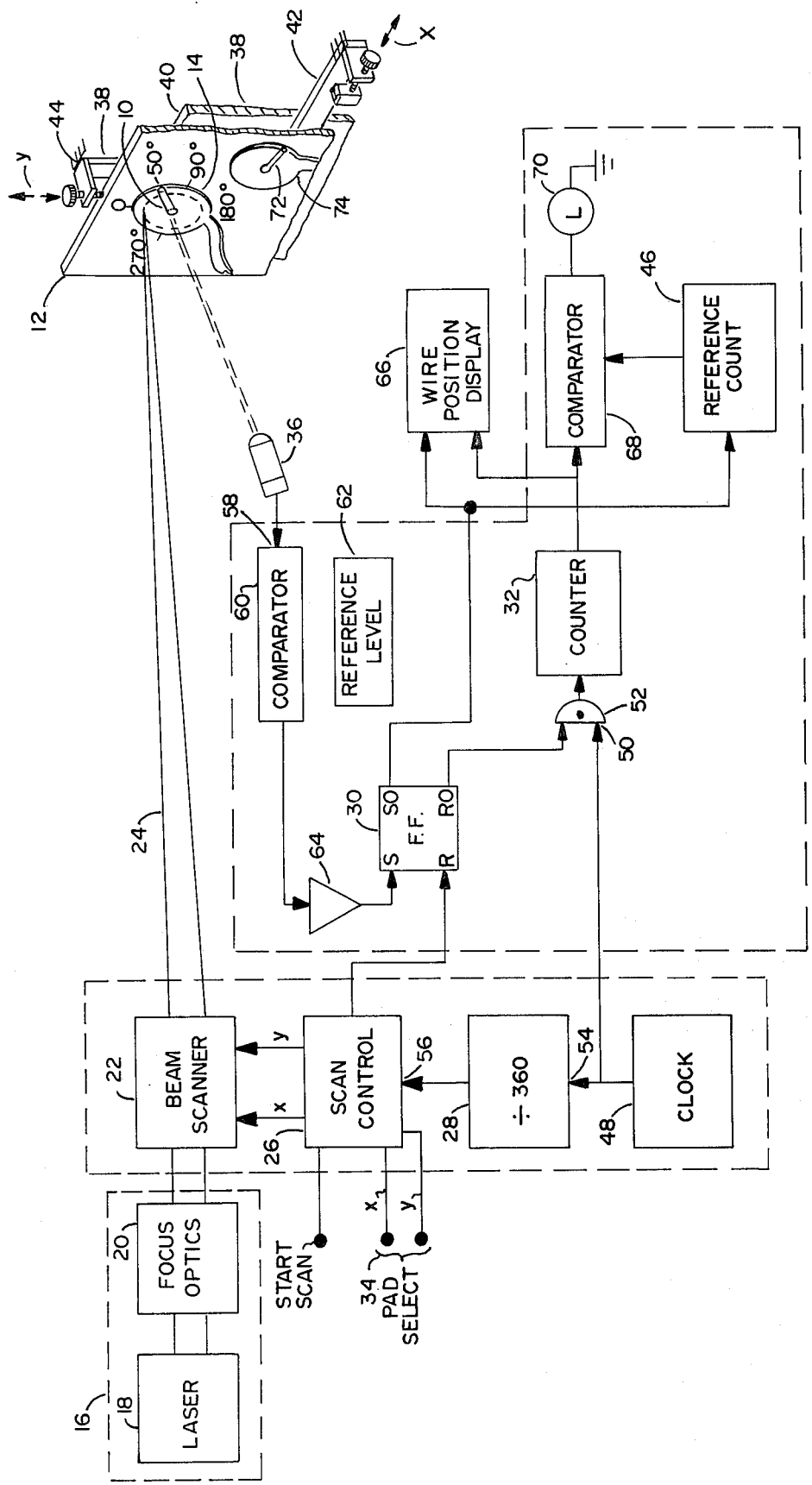
FIG. 1 is a schematic illustration of one embodiment of the invention, particularly illustrating the detection of wire positioning, lead orientation on a solder pad, and which is adapted for automatic control.

FIG. 1 shows a basic form of the invention as employed to determine whether a wire lead 10 on a printed circuit board or card 12 is correctly positioned on solder pad 14. The description of components not readily appreciated from their labels are as follows:

Laser assembly 16 consists of laser 18 and related optics 20 to produce a very small point of light, 5 to 10 microns when projected onto printed circuit board 12, the board being positioned at the focal point of the optics of the laser assembly.

Beam scanner 22 is conventional and consists of X and Y axis galvanometer-operated mirrors through which laser beam 24 is projected. Thus, an X axis mirror, responsive to an X signal, deflects the beam left and right; and a Y axis mirror, responsive to a Y input signal, deflects the beam up and down.

Scan control 26 includes a signal generator or generators which, conventionally, responsive to each pulse from divider 28, provides as each of two outputs one cycle of a sinusoidal-shaped electrical signal, the outputs being phase displaced 90 degrees to each other. These are supplied to beam scanner 22 as X and Y galvanometer operational signals to thus achieve the circular scan illustrated in FIG. 1. Scan control 26 also includes an electronic switch which, responsive to an input "start scan", turns "on" or enables the operation of scan control 26. Scan control 26 further includes a location detector which senses a peak or minimum "plus" excursion of the Y generator (0 degree location) and provides a reset input to flip flop 30 to initiate counting by counter 32, representative of the angular travel of beam 24. Scan control 26 further includes means for combining X and Y biases applied to "pad select" inputs 34 and with the like labelled cyclical signals, whereby beam 24 may be centered for circular scanning about any solder pad or other point on board 12.

For purposes of illustration, printed circuit board 12 is only partially shown, illustrating in exaggerated dimensions the solder pads, with respect to which wire leads are connected and are to be checked for annular position.

Light detector or sensor 36 is of a type adapted to particularly detect the wave length of light of laser 18. The relative orientation of the incident laser beam, the face of printed board 12, and the position of detector 36 are such that detector 36 will receive a substantial scattering of light as the laser beam is scanned over the portion of the printed board to be examined.

A board or card mounting fixture 38 includes frame 40, upon which is attached two movable holders 42 and 44, holder 42 being adapted to be adjustably moved horizontally, and holder 44 being adapted to be adjustably moved vertically. Board 12 is actually gripped by holder 44, which is mounted on holder 42; and holder 42 is in turn mounted on frame 40, thus providing X and Y manipulation of printed boards. This in turn may be automated via the use of a linear actuator.

Reference count device 46 is a counter in which a desired count is stored and which is supplied as an output upon being interrogated. Typically, it would be readily settable to any desired count within the range of operation of the system 360 counts, as illustrated, representative of a 360-degree circular scan of laser beam 24.

OPERATION

It will be assumed that wire lead 10 on printed circuit board 12 should be positioned at an angular position of 180 degrees, but in error is positioned at 50 degrees, as shown. It is to be pointed out that the angular position of a lead is quite significant in order to properly secure a component to the board and to leads of other components so as to prevent unwarded conductive paths upon soldering of a board, e.g., solder bridges.

Reference count device 46 is set to indicate the required position of lead 10, in this case being a count of 180, representative of 180 degrees.

Biasing inputs are supplied, as necessary, such that beam 24 will be positioned at the center of pad 14 with no cyclical input voltages present.

Clock 48, which typically operates at a frequency of 10,800 Hertz, provides a pulse output at this rate to input 50 of AND gate 52 and to input 54 of divide-by-360 divider 28. A thus divided pulse rate is then applied to input 56 of scan control 26 which, with a "start scan" input present, causes X and Y generators to provide X and Y inputs to beam scanner 22. When the Y scan voltage reaches a maximum positive value (at the same time X scan voltage will be zero), beam scanner 22 will be moving the laser beam through the position labelled 0 degrees on printed circuit board 12, a reference position. At this instant, this maximum plus value of the Y scan voltage is detected by scan control 26, and a pulse is applied to the reset input of flip-flop 30. The reset output of flip-flop 30 enables AND gate 52, enabling clock pulses to be provided from clock 48 to counter 32, causing it to commence counting, it providing a full count of 360 corresponding to each cycle of output of each of the X and Y inputs of beam scanner 22, and thus a full count of 360 degrees coordinate with the movement of beam 24 360 degrees around pad 14 of printed circuit board 12.

As beam 24 moves about pad 14 before striking lead wire 10, its reflection from the pad is picked up by detector 36. Detector 36 initially provides a "normal" output which is fed to input 58 of comparator 60. A reference input equal to the normal or "no lead" output of detector 36 is fed from reference level device 62 to the input of comparator 60. Comparator 60 compares the levels of the two applied input signals and is adapted to provide an output when the inputs are significantly dissimilar, its output being provided to amplifier 64. Thus, there will be no output of comparator 60 to amplifier 64 until the beam is scanned to 50 degrees, corresponding to a count of 50, whereupon the difference in scattered energy return of load 10 and the surface of solder pad 14 produces a signal value significantly differing from that provided by reference device 62. The resulting significant output of comparator 60 is amplified by amplifier 64 and applied to the input of flip-flop 30. This causes flip-flop 30 to be set and the enable gate input of AND gate 52 removed, causing counter 32 to stop at the count of 50. This set output also gates "on" write position display 66, which then displays the now resting count 50 of counter 32 at the same time this set output is supplied as a gating pulse to reference count device 46, causing the reference count, 180 in this case, to be supplied to comparator 68, where it is compared with the "50" output of counter 32. Comparator 68 subtracts the two input counts. Since they are not equal, it provides an output which energizes alarm light 70. Thus, an operator is alerted to the error. By observing the display, he is informed of the position of the incorrectly oriented lead.

In the event that this is the only test to be performed on this board at its present stage of fabrication, the board is removed from holding fixture 38, and the next board to be tested is placed in the fixture and the test repeated. If it is desired to check other connections on the same printed board, such as, for example, the position of wire lead 72 upon solder pad 74, the beam would be repositioned with respect to that pad in one of several ways or a combination of them. The card may be mechanically positioned by X and Y holding fixtures 42 and 44 so that the beam strikes a path over a circular path as illustrated with respect to pad 14. Alternately, beam scanner 22 and laser 18 may be positioned as a unit so that the beam is appropriately positioned, or the beam scan signals may be biased as described above by application of appropriate direct current voltages to X and Y pad select inputs 34.

Figure 2:
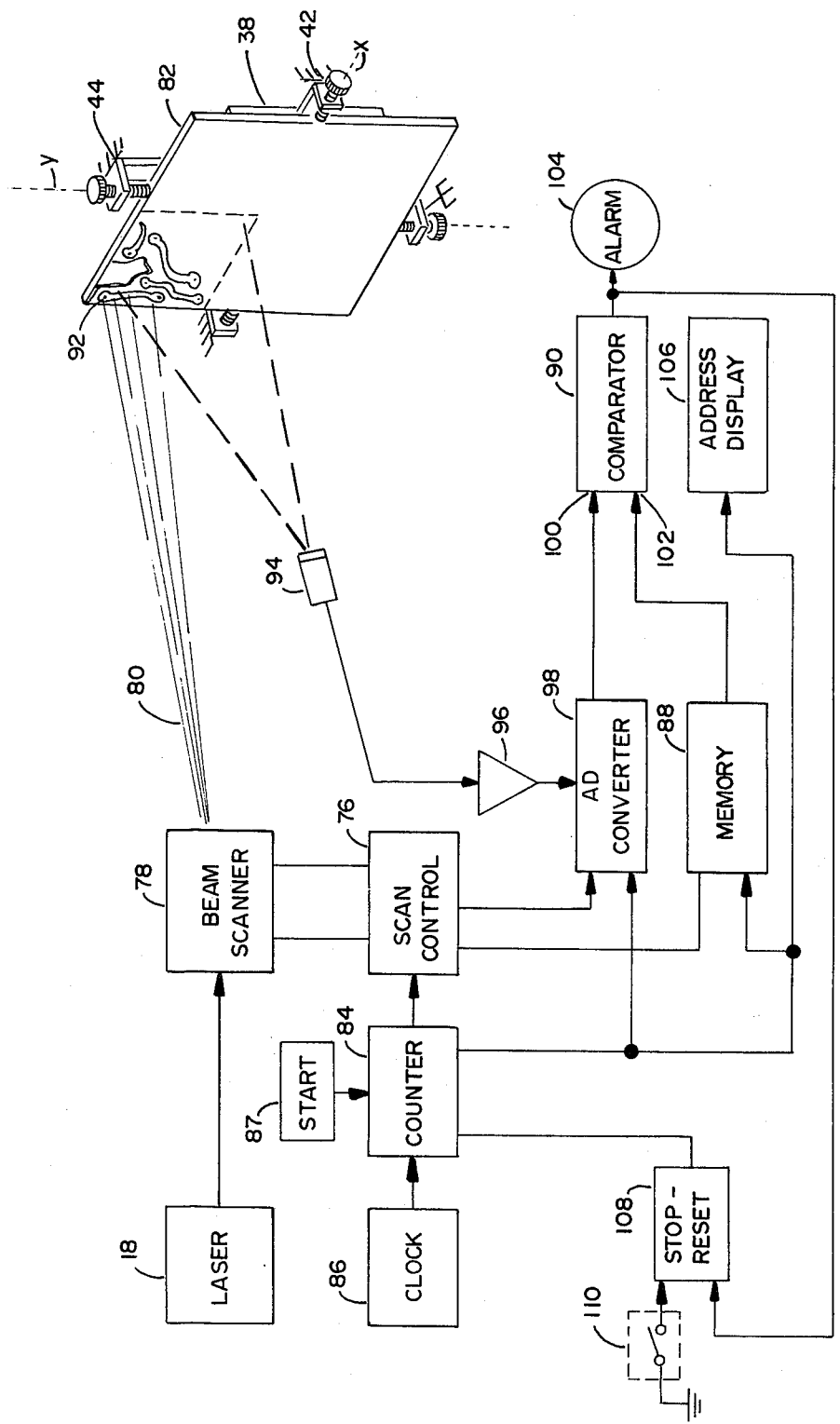
FIG. 2 is a schematic illustration of an embodiment of the invention, particularly adapted for computer control, wherein data from a properly printed reference circuit board would be stored in a memory and then compared with each like board which is to be tested.

FIG. 2 is illustrative of an alternate form of the invention. It uses a rectangular coordinate type sweep to scan a printed board, either partially or fully completed. Increments of data are thus obtained, representative of significant structural conditions of the overall board, observing component leads, soldering joints, etc. This data is compared with like obtained data from a previously and properly assembled card, the previously obtained data being stored in a memory. The description of components not previously described and not being susceptible to being readily understood from their designations follows:

Scan control 76 includes a digital-to-analog converter which decodes a digitally encoded address count from address counter 78 into an appropriate X coordinate voltage and Y coordinate voltage to cause beam scanner 78 to move beam 80 to a discrete X-Y defined address position on printed card 82. Thus, the face of the printed board may be regarded as having, for example, $4 \times 10^6$ addresses as if a grid made up of small squares or dots cover the board. Assuming a $3'' \times 3''$ size board, there might be 2,000 dot area addresses in each of 2,000 vertically arranged horizontal rows of dot areas. Thus, the addresses in the first row would be represented by count 1 to 2,000 and the second row by count 2,001 to 4,000, and so on.

Address counter 84 is simply a binary counter which is responsive to a clock input pulse from clock 86 and repetitively counts between 1 and N, representative of one count per dot or coordinate location on the card. Where it is not deemed necessary to examine each such coordinate location on a board, the counter would include a count only for locations of interest. In any event, scan control 76 would appropriately encode each count for a selected coordinate position. Where addresses are spaced, the beam scanner would slew between them at a fast rate. In addition to increased speed of operation where the whole card is not examined, the requirements for counting and encoding in a memory would be lessened.

Memory 88 has a memory location for each coordinate position of printed card which is of interest for testing. Each memory location is interrogatable by a discrete count from counter 84, and responsive thereto, it provides a digital value representative of reflected light from the same coordinate point on a properly constructed board, this data word being supplied in digital form to comparator 90.

OPERATION

First, it is assumed that memory 88 has been coordinately programmed with counter 84 and that there are data words stored in memory 88 representative of light reflections scanned from a properly constructed printed card against which card 88 is to be compared.

Clock 86 is gated by start switch 87 to commence supplying pulses at an appropriate selected rate to counter 84. With the receipt of the first pulse, counter 84 applies a first count to memory 88 and to scan control 76. Scan control 76 encodes this count into an analog value or values appropriate to move beam 80 to a first test location. The encoding might, for example, be representative of an X voltage of −5 and Y voltage of +5. In this manner, the galvanometer-operated mirrors of beam scanner 78 would position beam 80 in the indicated position, initially, for example, to point 92 on board 82. As a result, the reflection from point 92 is detected by detector 94, amplified in preamplifier 96, and supplied to analog-to-digital conver 98 where, conventionally, it is converted to the same digitally encoded form as data in memory 88. The resulting data word is applied to input 100 of comparator 90. At the same time, the count is supplied to memory 88, and this count identified location in memory 88 is interrogated, and a digital value for reflectance of a properly constructed board for this location, point 92, is supplied as a second input 102 to comparator 90. Comparator 90 then subtracts the inputs; and if there is a zero, that is, the inputs are substantially identical, indicating likeness between the boards, there is no output from comparator 90, no alarm signal is sent to alarm 104, nor is readout 106 enabled. Counter 84 simply steps on to a second count, and the process is repeated for the second input location to be examined and compared. In the event that in this instance the value of reflectance detected by detector 94 does not correspond to the value of memory 88, comparator 90 provides an output which operates alarm 104, provides a trigger to stop-reset 108, an output of which stops counter 84 at the instant count, and gates "on" display 106 which displays the count from counter 84 to thus signal the occurrence of a fault and the identity of its location.

After noting the error, the operator would cause scanning to restart by operating "stop interrupt" 110, a momentary switch. Scanning would then continue automatically unless and until a fault was again detected on board 82. When a total count occurs, counter 84 turns off and the test is completed. If desired, the completion of the count for a test is indicated by detecting the final count and displaying it on display 106.

Figure 3:
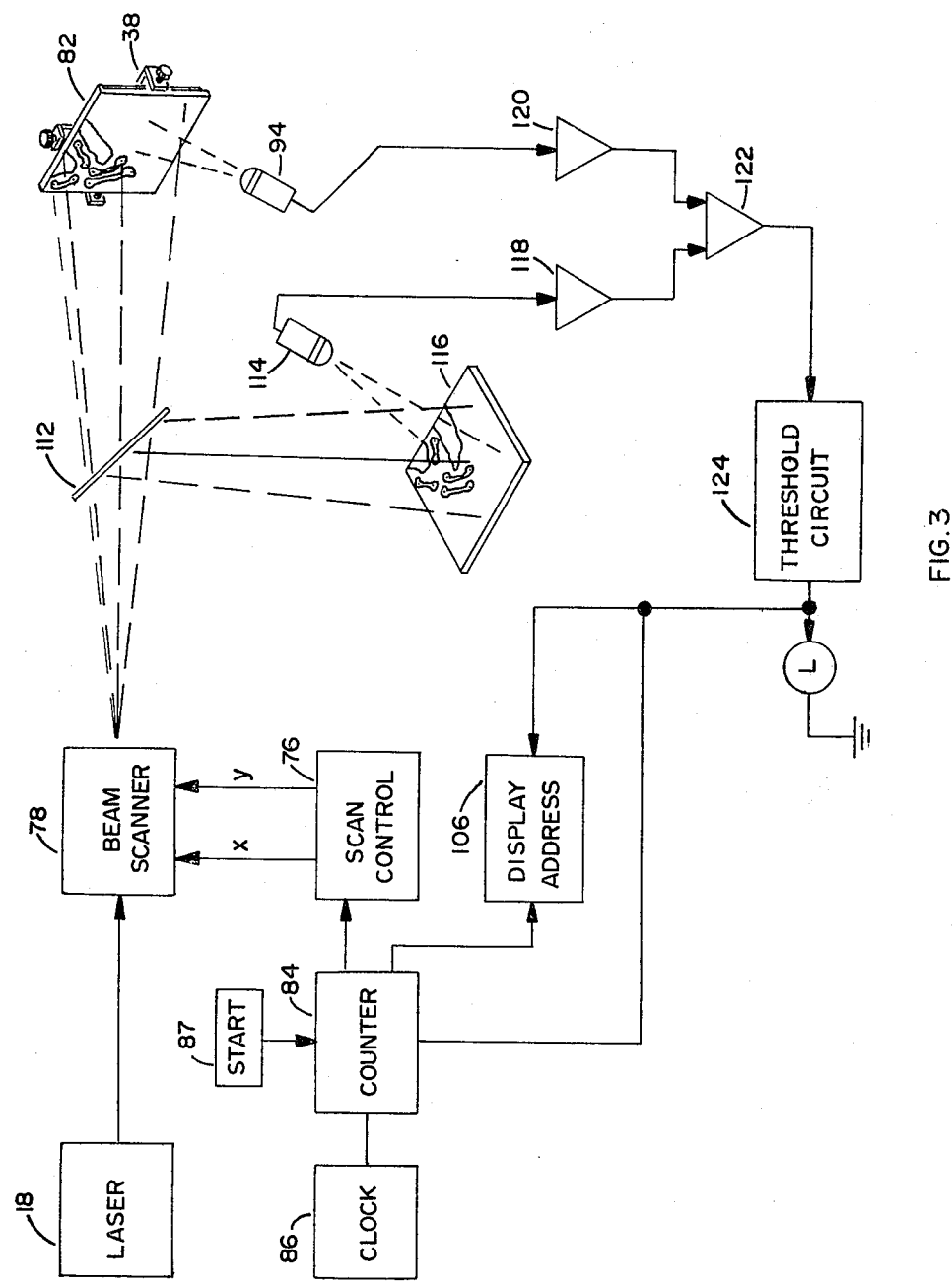
FIG. 3 is a schematic illustration of still another embodiment of the invention, one in which the reflected correlation pattern of a reference printed circuit board is optically compared with each like board to be tested.

FIG. 3 illustrates still another alternate form of the invention. In this case, an optical correlation is made between a properly constructed printed circuit board and a board being tested. Both are simultaneously scanned and scattered intensity signature values compared and faults thus noted. Thus, additionally, beam splitter 112 is interposed between beam scanner 78 and printed circuit board 82 to be tested. Beam splitter 112 is positioned to reflect a portion of the beam from beam scanner 78 in register onto a reference printed circuit board. A second detector 114 is then oriented and positioned with respect to reference board 116 in the same manner as detector 94 with respect to board 82 in FIG. 2. Clock 86, counter 84, scan control 76, and display address 106 operate in the same fashion as like units of the system shown in FIG. 1.

OPERATION

With printed boards 116 and 82 positioned in the register, clock 86 is operated "on", and counter 84 is caused to commence supplying counts to scan control 76 and display address 106. As each board is scanned, in register, at discrete locations of interest, the scattered energy return from boards 116 and 82 are detected by detectors 114 and 94 and are supplied to preamplifiers 118 and 120. Any difference between scattered energy returns is detected by differential amplifier 122, which then provides an output to threshold circuit 124. Threshold circuit 124 is simply a level sensor which determines the amount of difference permissible before a board would be deemed out of tolerance; and when this level is exceeded, it provides an output to alarm 126 which provides a digital signal output, which causes a light or other alarm to signal the defect. This output of threshold circuit 124 is also supplied to counter 84 to stop counter 84 and to display address 106. As a result, counter 84 is stopped, and display address 106 is enabled, causing the last count on counter 84 to be displayed, thus indicating the position of the fault.

While the system illustrated in FIG. 1 is described as employing circular scanning of beam scanner 22, and the systems illustrated in FIGS. 2 and 3 as employing rectangular scanning, it is to be appreciated that each of the systems may employ other types, as suggested above. For example, beam scanner 78 of FIGS. 2 and 3 might be scanned in a programmed manner as described to direct the laser beam to the center of a solder pad on the board. When this has been accomplished, beam scanner 78 would be caused to go into a circular or spiral scan mode to particularly scan the solder pad in this fashion in order to determine a lead position.

Having thus described our invention, what is claimed is:

1. An electrical circuit board testing system comprising:
   a circuit board having a plurality of connective holes therethrough and electrically conductive leads of components extending along said board in discrete and varied directions to said holes;
   positioning means for holding and positioning a said printed circuit board under test at a precise position, wherein a face of said board to be examined is unobscured;
   a counter;
   illumination means, including a laser and focusing optics, for focusing a beam of laser light onto the face of said printed circuit board held by said positioning means;
   scanning means responsive to a discrete count from said counter for positioning said beam along selected paths which include paths substantially normal to and across radial lines from said holes and accordingly substantially normal to said leads on said board;
   detection means spaced from said printed circuit board and spaced from and to the side of said beam for sensing the amplitude of scattered laser light from separate discrete regions of said board as said board is scanned and for providing discrete electrical outputs, each representative of the amplitude of scattered light from a discrete region of said board as it is scanned; and reference means including an electrical memory having discrete electrical values, representative of discrete amplitude values of scattered light from a reference circuit board resulting from exposure of said reference circuit board along like said selected paths, said values being stored in said memory and located by discrete counter addresses, and said reference means including means for reading out said discrete electrical values responsive to said counter;

whereby selected paths, or a selected series of paths, of scanning may be effected in any direction and at any location on said board, and the existence and location of a conductor on the surface of said board detected and compared with the existence or location of a conductor on said reference board which lies substantially normal to a said path.

2. A printed circuit board tester as set forth in claim 1 further comprising digital display means responsive to said detection means and said counter for displaying a count occurring when signals from said detection means and said reference means are not substantially identical.

* * * * *